(12) United States Patent
Matsuya et al.

(10) Patent No.: US 11,041,864 B2
(45) Date of Patent: Jun. 22, 2021

(54) METHOD FOR PREDICTION OF PROGNOSIS OF SEPSIS (75) Inventors: Takeshi Matsuya, Tokyo (JP);
Yoshikazu Okamura, Tokyo (JP); Ralf Thomae, Gauting (DE); Eberhard Spanuth, Heidelberg (DE); Boris Ivandic, Munich (DE); Kamon Shirakawa, Tokyo (JP); Shigeatsu Endo, Iwate (JP)

(73) Assignees: LSI MEDIENCE CORPORATION, Tokyo (JP); MOCHIDA PHARMACEUTICAL CO., LTD., Tokyo (JP)

(*) Notice: Subject to any disclaimer, the term of this patent is extended or adjusted under 35 U.S.C. 154(b) by 770 days.

(21) Appl. No.: 13/979,133

(22) PCT Filed: Jan. 10, 2012

(86) PCT No.: PCT/JP2012/050226
§ 371 (c)(1),
(2), (4) Date: Jul. 10, 2013

(87) PCT Pub. No.: WO2012/096245
PCT Pub. Date: Jul. 19, 2012

(65) Prior Publication Data
US 2013/0288276 A1  Oct. 31, 2013

(30) Foreign Application Priority Data
Jan. 11, 2011 (JP) .............................. JP2011-003016

(51) Int. Cl.
*G01N 33/53* (2006.01)
*G01N 33/68* (2006.01)

(52) U.S. Cl.
CPC ............ *G01N 33/6893* (2013.01); *G01N 2333/70596* (2013.01); *G01N 2800/26* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 4,444,879 | A * | 4/1984 | Foster | G01N 33/545 422/400 |
| 5,484,699 | A * | 1/1996 | Bouma | C12Q 1/708 435/5 |
| 8,444,932 | B2 * | 5/2013 | Spanuth | G01N 33/6893 422/430 |
| 8,450,463 | B2 | 5/2013 | Bergmann | |
| 2005/0148029 | A1 | 7/2005 | Buechler et al. | |
| 2005/0164238 | A1 | 7/2005 | Valkirs et al. | |
| 2005/0196817 | A1 * | 9/2005 | Kingsmore | G01N 33/6893 435/7.92 |
| 2006/0068445 | A1 | 3/2006 | Furusako et al. | |
| 2006/0127912 | A1 * | 6/2006 | Pachot | C12Q 1/6883 435/6.16 |
| 2007/0092911 | A1 | 4/2007 | Buechler et al. | |
| 2007/0106067 | A1 * | 5/2007 | Furusako | C07K 14/70596 530/388.22 |
| 2007/0281300 | A1 * | 12/2007 | Russell | C12Q 1/6883 435/6.11 |
| 2008/0050832 | A1 | 2/2008 | Buechler et al. | |
| 2009/0004755 | A1 | 1/2009 | Lee et al. | |
| 2009/0029396 | A1 | 1/2009 | Furusako et al. | |
| 2009/0203052 | A1 | 8/2009 | Furusako et al. | |
| 2010/0240078 | A1 | 9/2010 | Lee et al. | |
| 2011/0086381 | A1 * | 4/2011 | Naito | C07K 14/70596 435/29 |
| 2012/0094314 | A1 | 4/2012 | Bahrami et al. | |

FOREIGN PATENT DOCUMENTS

| | | | |
|---|---|---|---|
| CN | 1918473 A | 2/2007 | |
| JP | 2005-106694 | 4/2005 | |
| WO | WO 2014102333 A1 * | 7/2014 | ............. G01N 33/68 |

OTHER PUBLICATIONS

Takahashi et al. ("Severity assessment of sepsis by determination of the soluble CD14 subtype using the POC test" Medical Postgraduates vol. 48 No. I, 2010, p. 25-27).*
Spanuth et al. ("Diagnostic and prognostic value of presepsin (soluble CD14 subtype) in emergency patients with early sepsis using the new assay PATHFAST Presepsin" 21st International Congress of Clinical Chemistry and Laboratory Medicine, IFCC—WorldLab—EuroMedLab, Berlin, May 15-19, 2011).*
Burgmann et al. ("Increased Serum Concentration of Soluble CD14 Is a Prognostic Marker in Gram-Positive Sepsis" Clinical Immunology and Immunopathology vol. 80, No. 3, September, pp. 307-310, 1996, Article No. 0128).*
Aalto et al. ("Monocyte CD14 and soluble CD14 in predicting mortality of patients with severe community acquired infection" Scandinavian Journal of Infectious Diseases, 2007, 39: 596-603).*
Pierrakos et al. ("Sepsis biomarkers: a review" Pierrakos and Vincent Critical Care 2010, 14:R15).*
Van Der Vekiens et al., Human and equine cardiovascular endocrinology: beware to compare, Cardiovascular Endocrinology 2013, vol. 2, No. 4, pp. 67-76.*
Torzewski et al., Animal Models of C-Reactive Protein, Hindawl Publishing Corporation, Mediators of Inflammation, vol. 2014, Article ID 683598, 2014, pp. 1-7.*
Chen et al., Risk stratification of severe sepsis patients in the emergency department, Emerg Med J 2006, 23, pp. 281-285.*
Nguyen et al., Severe Sepsis and Septic Shock: Review of the Literature and Emergency Department Management Guidelines, Annals of Emergency Medicine, vol. 48, No. 1, Jul. 2006, pp. 28-55. (Year: 2006).*

(Continued)

*Primary Examiner* — Gary Counts
(74) *Attorney, Agent, or Firm* — Kilpatrick Townsend & Stockton LLP (57) ABSTRACT

Disclosed is a prediction method for the prognosis of sepsis comprising measuring an sCD14-ST level in a sample. sCD14-ST, to be measured in the present invention, is a marker superior to procalcitonin, known as a marker to predict the prognosis in sepsis patients.

11 Claims, 3 Drawing Sheets

Specification includes a Sequence Listing.

(56) References Cited

OTHER PUBLICATIONS

Novotny et al., Use of procalcitonin for early prediction of lethal outcome of postoperative sepsis, The American Journal of Surgery 194, 2007, pp. 35-39. (Year: 2007).*

Joannidis, Michael Continuous Renal Replacement Therapy in Sepsis and Multisystem Organ Failure, Seminars in Dialysis, vol. 22, No. 2, (Mar.-Apr. 2009, pp. 160-164. (Year: 2009).*

Shigeatsu Endo et al.; Usefulness of Soluble CD 14 Subtype which as is a New Diagnostic Marker for Sepsis; Japan Journal of Critical Care for Endotoxemia; 2005; vol. 9, No. 1, pp. 46-50.

Yasunori Yaegashi et al.; Evaluation of a newly identified soluble CD14 subtype as a marker for sepsis; J. Infect Chemother; 2005; 11:234-238.

Gaku Takahashi et al.; Severity assessment of sepsis by determination of the soluble CD14 subtype using the POC test; Medical Postgraduates; 2010; vol. 48, No. 1, pp. 25-27.

Stephan Harbarth et al.; Diagnostic Value of Procalcitonin, Interleukin-6, and Interleukin-8 in Critically Ill Patients Admitted with Suspected Sepsis; Am. J. Respir. Crit. Care Med.; 2001; 164:396-402.

International Search Report of PCT/JP2012/050226 dated Mar. 27, 2012.

Aalto et al., "Monocyte CD14 and soluble CD14 in predicting morality of patients with severe community acquired infection," Scandinavian Journal of Infectious Diseases, Jan. 2007, vol. 39(6-7), pp. 596-603.

Burgmann et al., "Increased Serum Concentration of Soluble CD14 is a Prognostic Marker in Gram-Positive Sepsis," Clinical Immunology and Immunopathology, Sep. 1996, vol. 80(3), pp. 307-310.

European Search Report, dated Oct. 24, 2014, EP application No. 12733987.7, 4 pages.

Sato, Nobuhiro; Therapeutic Research, 25(8):1689-1694, 2004, Englsih portions only.

Endo, S. et al., "Rapid Diagnostic Method for Sepsis," ICU & CCU 29(1):21-26, 2005, English portions only.

Minne, L. et al., "Evaluation of SOFA-based models for predicting mortality in the ICU: A systematic review," Critical Care, BioMed Central Ltd., London, GB, vol. 12, No. 6, Dec. 17, 2008, p. R161.

* cited by examiner

METHOD FOR PREDICTION OF PROGNOSIS OF SEPSIS

CROSS-REFERENCE TO RELATED APPLICATIONS

This application is a national phase application under 35 U.S.C. 371 claiming priority to PCT/JP2012/050226, filed Jan. 10, 2012, which application claims priority to JP 2011-003016, filed Jan. 11, 2011, the teachings of which are hereby incorporated by reference in their entireties for all purposes.

TECHNICAL FIELD

The present invention relates to a method for predicting the prognosis of sepsis and a kit for conducting the method.

BACKGROUND ART

Diagnosis of sepsis by measuring the level of sCD14-ST in a sample has been disclosed (Non-Patent Document 1, Patent Document 1). In addition, the measurement of sCD14-ST using a specific antibody thereto has also been disclosed (Patent Document 1, Patent Document 2). Further, a method for early detection and for assessing severity thereof has been disclosed (Patent Document 2, Non-Patent Documents 2 to 4). However, in these documents, it has only been disclosed that an assessment as to whether or not the state of the patient is severe at a certain point in time can be made, and also an assessment of whether or not the symptom is that of sepsis can be made immediately upon the onset of sepsis, and there is no assumption or disclosure that prognosis of sepsis from several days up to tens of days after the onset of sepsis can be predicted by measuring the sCD14-ST when the suspicion of sepsis has been raised.

Incidentally, besides the sCD14-ST, procalcitonin (PCT) is also known as a diagnostic marker for sepsis. It is thought that procalcitonin can be used not only to assess whether or not the symptom is that of sepsis at the time of measurement, but also to a prediction with respect to the severity level of sepsis, that is, prognosis (and especially risk of death) (Non-patent Document 5), and is approved as a marker capable of predicting the severity level of sepsis by the Food and Drug Administration (FDA) in the United States.

CITATION LIST

Patent Literature

[Patent literature 1] Japanese Patent No. 4040666
[Patent literature 2] Japanese Unexamined Patent Publication (Kokai) No. 2005-106694

Non-Patent Documents

[Non-Patent literature 1] J. Infect. Chemother. 2005; 11: 234-238.
[Non-Patent literature 2] Medical Postgraduates 2010; 48: 25-27.
[Non-Patent literature 3] Therapeutic Research 2004; 25: 1689-1694.
[Non-Patent literature 4] ICU and CCV 2005; 29: 21-26.
[Non-Patent literature 5] Am. J. Respir. Crit. Care Med. 2001; 164: 396-402.

SUMMARY OF INVENTION

Technical Problem

When sepsis is suspected, a swift decision of an appropriate treatment strategy is required. An object of the present invention is to provide a novel marker which can be used for prognostic prediction and which is superior to procalcitonin, known as a marker to predict the prognosis in sepsis patients.

Solution to Problem

During the intensive and extensive investigations, in order to solve the aforementioned problem, the present inventors have discovered that the prognosis of sepsis regarding how severe it will be (so-called risk stratification) from several days up to tens of days after the onset of sepsis, or the risk of death can be predicted by measuring the level of sCD14-ST in the sample within 72 hours after the suspicion of sepsis has been raised, from the measured values or the level, and consequently completed the present invention.

The present invention relates to the following:

[1] A prediction method for the prognosis of sepsis characterized by measuring an sCD14-ST level in a sample;

[2] The prediction method according to [1], in which the sCD14-ST level is measured within 72 hours from a point in time where suspicion of sepsis has been raised;

[3] The prediction method according to [1], in which a prognostic prediction is a prediction for the development of septic complications;

[4] A measuring method for an sCD14-ST level in a sample in order to predict the prognosis of sepsis;

[5] The measuring method according to [4], in which the sCD14-ST level is measured within 72 hours from a point in time where suspicion of sepsis has been raised;

[6] The measuring method according to [4], in which the sCD14-ST level is measured after treating sepsis;

[7] The measuring method according to [4], in which a prognostic prediction is a prediction for the development of septic complications;

[8] A method for predicting the prognosis of sepsis which includes a step of measuring an sCD14-ST level in a sample collected from a patient with suspected sepsis or a sepsis patient, and a step of diagnosing poor prognosis when the sCD14-ST level is higher compared to that of a healthy individual;

[9] The method according to [8], in which the sCD14-ST level is compared with a threshold value, which is determined in advance, in the diagnosis step;

[10] The method according to [8], in which the sCD14-ST level is correlated with each quantile group, which is determined in advance, in the diagnosis step;

[11] The method according to any one of [1] to [10], in which the sCD14-ST level is measured by an immunological measuring method; and

[12] A kit for predicting the prognosis of sepsis which includes (a) an antibody specific to sCD14-ST, (b) standard data which shows a correlation between the sCD14-ST level in a sample and prognosis, and (c) an instruction manual.

Herein, the term "human sCD14-ST" (also referred to as Presepsin (registered trademark)) as used herein refers to the "soluble CD14 antigen of the first aspect" disclosed in Japanese Patent No. 4040666, and more specifically refers to a soluble CD14 antigen with the following characteristics 1) to 3):

1) Molecular weight of 13 ±2 kDa measured by the SDS-PAGE under a nonreducing condition;
2) Inclusion of an amino acid sequence of SEQ ID NO: 1 within the N-terminal sequence; and
3) Binds specifically to an antibody, which is prepared by using a peptide consisted of 16 amino acid residues of SEQ ID NO: 2 as an antigen.

The term "sCD14-ST" as used herein means human sCD14-ST, unless otherwise specified.

```
SEQ ID NO: 1:
Thr Thr Pro Glu Pro Cys Glu Leu Asp Asp Glu
1               5                   10

SEQ ID NO: 2:
Arg Val Asp Ala Asp Ala Asp Pro Arg Gln Tyr Ala Asp Thr Val Lys
1               5                   10                  15
```

The term "sepsis" refers to a state where, for example, one satisfies two or more criteria out of the following four criteria, which are the components for the diagnosis of systemic inflammatory response syndrome (SIRS), in addition to the presence of infection [Chest 1992; 101 (6): 1644-1655].
1) Body temperature >38° C. or <36° C.;
2) Heart rate>90 per minute
3) Respiration rate>20 per minute or $PaCO_2$>32 torr
4) White blood cell count>12,000, <4,000/$m^3$ or immature leukocytes>10%.

The aforementioned "infection" includes infections by bacteria, fungi, parasites or viruses.

The method of verifying the presence of infection is not particularly limited, and examples thereof include, in addition to the commonly conducted blood culture, gene identification methods (such as PCR and RP-PCR), diagnostic imaging, ultrasonic diagnosis, endoscopy and biopsy [Am. J. Infect. Control 1988; 16: 128-440].

The term "severe sepsis" refers to the sepsis symptom that is further accompanied by the organ hypoperfusions that are apparent from the signs of at least one organ failure (for example, hypoxemia, oliguria, metabolic acidosis or a cerebral anomaly).

The term "septic shock" refers to the severe sepsis symptom that is further accompanied by the hypotension that is apparent from a systolic blood pressure of <90 mmHg or the necessity of drug intervention for maintaining blood pressure.

Examples of the "complications of sepsis" include multiple organ dysfunction syndrome (MODS), disseminated intravascular coagulation syndrome (DIC), acute respiratory distress syndrome (ARDS) and acute kidney insufficiency (AKI). The possibility for inducing the complications of sepsis increases as the severity of sepsis rises to severe sepsis and then to septic shock. For example, the "multiple organ dysfunction syndrome (MODS)" is a syndrome in which two or more vital organs cause functional disorder at the same time, and is identified in association with the SIRS criteria.

The term "sepsis" used herein includes the sepsis symptom associated with the end stage of sepsis and the onset of "severe sepsis", "septic shock" and "complications of sepsis" described above, as well as all stages of sepsis, which is not limited.

Although sepsis can be treated by the use of antibiotics or supportive therapy, it remains a serious cause of mortality. According to an estimation in a recent study, 751,000 cases of severe sepsis occur every year in the United States, and the mortality rate thereof is 30 to 50%. The specialists of intensive care or infectious diseases who belong to the Society of Critical Care Medicine (SCCM), the European Society of Intensive Care Medicine (ESICM) and the ISF (International Sepsis Forum) have set up an international program called the "Surviving Sepsis Campaign (SSC)" in 2002 in order to reduce the mortality rate of severe sepsis by 25% during the next 5 years, and the Surviving Sepsis Campaign guidelines (SSCG) have been prepared as part of the approach. This guideline is published as a guideline for the diagnosis/treatment of severe sepsis which is based on the first evidence from 2004, and the revised edition thereof is published in 2008 [Crit. Care. Med. 2008; 36: 296-327]. These guidelines are based on the initial fluid therapy (early-goal directed therapy) for severe sepsis, or the like [New Engl. J. Med. 2001; 345: 1368-1377].

Examples of the treatments for sepsis described in the present guidelines include the use of antimicrobial agents, fluid therapy, vasoconstrictors, cardiac drugs, steroid therapy, blood preparations, blood sugar control, blood purification methods [such as continuous hemofiltration (CHF), continuous hemodiafiltration (CHDF) and hemodialysis (HD)] and surgery (such as abscess drainage and removal of infected necrotic tissues), in addition to the endotoxin adsorption therapy with polymyxin (PMX) and γ-globulin preparations [Crit. Care Med. 2008; 36: 296-327]. The therapeutic agents for sepsis are not limited to the drugs described above, and it is possible to refer to, for example, "Therapeutic Drugs of Today—Explanations and Manuals 2006" edited by Yutaka MIZUSHIMA and published in 2006 by Nankodo Co., Ltd., or the like.

Herein, the term "prognosis" refers to the progress of a patient after the suspicion of sepsis has been raised. Examples of prognostic risks include an artificial respiration treatment, transfer to an intensive care unit (ICU), dialysis, onset of complications and death, and these risks can be identified, as compared to the conventionally known markers. Especially, the risks for dialysis and death can be predicted with high accuracy.

Herein, the "prediction" of prognosis refers to the prediction for the progress of a patient after the suspicion of sepsis has been raised. The "risk stratification" is one of the available techniques for this "prediction". The "risk stratification" is a technique to classify and differentiate patients based on sepsis severity. Classification based on the severity can be carried out due to the extent of the pathological state, such as high, moderate and low, or due to the type of pathological state, such as SIRS, initial sepsis, severe sepsis and septic shock. In addition, it is also possible to classify the risk of death or rate of survival.

Advantages Effects of Invention

According to the method of the present invention, the prognosis of sepsis, for example, the prognostic severity, death risk or survival rate can be predicted at an early stage of the onset of sepsis. The accuracy of the prediction is far superior compared to that using procalcitonin, which has been approved by the FDA in the United States as a marker capable of predicting the severity level of sepsis.

Additionally, according to the method of the present invention, an appropriate treatment strategy can be developed in accordance with the predicted prognosis as described above, and the prognosis of sepsis, for example, the prognostic severity, death risk or survival rate can be predicted even after the treatment. In other words, the therapeutic effects are also predictable.

Moreover, according to the method of the present invention, the occurrence of sepsis complications can be predicted based on the predicted prognostic severity.

Furthermore, the kit of the present invention can be used for the method of the present invention.

DESCRIPTION OF EMBODIMENTS

In the prediction method or measuring method of the present invention (hereafter, referred to as the method of the present invention), the sCD14-ST level in a sample collected from a subject, especially a patient suspected of having sepsis or a sepsis patient is measured. Such subjects also include the patients of infectious disease that require an antimicrobial treatment and the deteriorating patients with infection.

The sCD14-ST measuring method itself is already known, and the measurement can be carried out by various analytical methods for proteins, for example, an immunological assay using an antibody or a biochemical assay such as electrophoresis, and an autoanalyzer for a clinical laboratory test can also be used. Analytical methods that use the materials with similar properties to those of the antibodies, such as the RNA aptamers, form a part of the present invention as well.

For example, in Japanese Patent No. 4040666, a method for measuring the level of human sCD14-ST, more specifically, a polyclonal antibody (S68 antibody) prepared by using a peptide consisting of 16 amino acid residues of SEQ ID NO: 2 (the S68 peptide described in Japanese Patent No. 4040666) as an antigen, and a sandwich-type enzyme immunoassay (EIA), which uses a combination of a monoclonal antibody (F1146-17-2 antibody) and a monoclonal antibody prepared using CD14 as an antigen (for example, F1031-8-3 antibody, F1106-13-3 antibody, or the like) [Example 7-(1) in Japanese Patent No. 4040666] have been disclosed, and these can be applied to the method of the present invention.

In addition, as shown in the Examples described later, it is also possible to carry out the measurement of the sCD14-ST level, using an automated chemiluminescent immunoassay analyzer (PATHFAST; manufactured by Mitsubishi Chemical Medience Corporation), or by a chemiluminescent enzyme immunoassay using magnetic particles.

There are no particular limitations on the sample used in the method of the present invention as long as the sCD14-ST level can be measured. For example, blood samples (for instance, whole blood, plasma or serum), urine, lymph, cerebrospinal fluids and other body fluids can be used.

In the method of the present invention, increase in the sCD14-ST level in the sample is adopted as an indicator of poor prognosis. For example, as shown in Example 2 described later, the survival rate declines as the sCD14-ST level increases, and the survival rate was 35% in the patient group with high sCD14-ST values (group IV; 1,858 pg/mL or more). As described above, in the method of the present invention, when the sCD14-ST level shows a high value, it is possible to judge that the state of the prognosis of sepsis is poor and the death risk is high. On the other hand, when the sCD14-ST level shows a low value, it is possible to judge that the state of the prognosis of sepsis is favorable and the death risk is low. For example, it is possible to judge that the state of the prognosis of sepsis is poor if the sCD14-ST level in the sample is higher than a quantile value (for example, median) for that of the healthy individuals. In addition, it is possible to employ statistical techniques such as the Cox regression and the logistic regression for this analysis. Moreover, it is possible to predict the prognostic severity of sepsis in accordance with the sCD14-ST level. For the criteria, a "threshold value" prepared in advance can be used.

In the method of the present invention, although the threshold value for the sCD14-ST level in order to predict the prognosis is expected to vary depending on various conditions, such as sex and age, the threshold value for the judgment can be determined for those skilled in the art by appropriately selecting a suitable population that corresponds to the subjects and statistically processing the data acquired from the population. With the aforementioned population, a group of healthy individuals, a sepsis group, septic groups of different pathological level, septic groups of different pathological types, or the like can be selected. In Example 4 described later, an optimal cutoff value of 1,108 pg/mL (sensitivity=78%, specificity=66%) has been defined by the receiver operating characteristic (ROC) analysis shown in FIG. 4. In the method of the present invention, it is possible to automatically predict the prognosis of sepsis without consulting a doctor by determining the threshold value for the judgment, and comparing the measured sCD14-ST level in the sample with the threshold value for the judgment.

In the method of the present invention, although the time for sample collection is preferably at a stage where suspicion of sepsis has been raised or a stage after the treatment, the sample may be collected over time after the patient has been admitted. More specifically, the sample may be collected, for example, when the patient is admitted to a hospital or an emergency ward for the first time, before and/or after the treatment in an intensive care unit, 24 hours after the treatment, 48 hours after the treatment, and 72 hours after the treatment.

According to the first aspect of the method of the present invention, the prognosis of sepsis can be predicted at an early stage of the onset of sepsis. The early stage of the onset of sepsis also includes a stage where the suspicion of sepsis is raised.

The stage where the suspicion of sepsis is raised refers to an early stage of sepsis, which is, for example, prior to a stage where the conventional clinical symptoms sufficiently support a clinical suspicion of sepsis. Since the method of the present invention can be used for detecting sepsis before the confirmation of sepsis using a conventional diagnostic guideline, in a specific embodiment, the disease state of the patient in an early stage of sepsis can be confirmed at a much earlier date, as compared to the point in time where the signs of sepsis are clinically apparent, that is, the stage where the clinical suspicion of sepsis is raised by a doctor based on clinical symptoms. More specifically, the stage where the clinical suspicion of sepsis is raised by a doctor within 72 hours after the patient has been transferred to a hospital, an ICU, or the like. An accurate mechanism by which the patient develops sepsis is not an important embodiment of the present invention. The method of the present invention is highly useful since the onset of sepsis can be detected independently of the origin of infection process, and can predict the prognosis thereof at a stage where the suspicion of sepsis is raised.

According to the second aspect of the method of the present invention, the prognosis of sepsis attributable to the therapeutic effects of sepsis can be predicted. Although the usage for the prediction of prognosis attributable to the therapeutic effects is not particularly limited, it may be used for monitoring the therapeutic effects as follows. For example, after the admission, in those cases where the sample was collected from the patient before the treatment, after the treatment and at a stage where the therapeutic effects become apparent, and also the obtained sCD14-ST level exceeded the preset threshold value in spite of the treatment, poor prognosis is predicted with no therapeutic effects. Moreover, in those cases where the sCD14-ST level, which was already higher than the threshold value at the time of admission, was reduced so as to become lower than the threshold value due to the treatment, favorable prognosis with certain therapeutic effects is predicted.

According to the third aspect of the method of the present invention, the development of sepsis complications can be predicted. Although the prediction for the development of sepsis complications is not particularly limited, it is predicted that the possibility of developing complications increases when the sCD14-ST level exceed the preset threshold value. In addition, it is predicted that the possibility of developing complications reduces when the sCD14-ST level is lower than the preset threshold value.

The kit of the present invention can be used for carrying out the method of the present invention and includes:

(a) an antibody specific to sCD14-ST;

(b) standard data which show a correlation between the sCD14-ST level in a sample and the prognosis; and (c) an instruction manual.

The aforementioned antibody used in the kit of the present invention may be either a monoclonal antibody or a polyclonal antibody. In addition, it is possible to use an antibody fragment that retains a specific binding capacity to sCD14-ST in the kit, for example, as the fragment Fab, Fab', F(ab')$_2$ or Fv.

Further, the aforementioned antibody can be used, as it is, in the kit, or can also be used in the kit in a suitable form based on the immunological technique to be employed, for example, by being fixed onto a latex carrier when employing a latex agglutination immunoassay, by being fixed onto magnetic particles when employing a highly sensitive measuring method using magnetic particles or the like, by being fixed onto a substrate when employing a method that uses a substrate, such as an immunochromatography, and by being labeled with labeling substances (for example, enzymes, fluorescent substances, chemiluminescent substances, radioactive isotopes, biotin, avidin) if necessary.

The aforementioned standard data included in the kit of the present invention are not particularly limited as long as they show a correlation between the sCD14-ST level in a sample and the prognosis, and examples thereof include the threshold value for the judgment, and the original data or statistically processed data for calculating the threshold value for the judgment. The standard data may be described in the aforementioned instruction manual or may be attached separately as a data sheet. In addition, the form of the attached document includes paper, electronic media such as CD-ROM and those downloaded from homepages or the like.

Moreover, there are no particular limitations on the aforementioned instruction manual included in the kit of the present invention as long as it refers at least to the relationship between the sCD14-ST level in the sample and the prognosis of sepsis. For example, in addition to the above reference, the instruction manual can include the explanation regarding the procedure for carrying out the immunological measurement that uses the kit of the present invention, the explanation regarding the procedure for predicting the prognosis based on the obtained measurement values, the precautions regarding the storage and handling of the kit per se, or the like.

EXAMPLES

Although the present invention will be described below in more detail through a series of Examples, the scope of the present invention is not limited by these Examples.

A prospective study for sepsis was conducted for registered emergency patients at a clinical site of one facility for a certain period of time. It should be noted that this test was conducted with the approval of the ethics committee. The patients registered for the test were men and women aged 18 or over who were admitted to an emergency hospital with signs of severe infection and who were also showing clear signs of sepsis or strongly suspected of having sepsis by satisfying two or more criteria out of the following 4 requirements.

1) Body temperature >38° C. or <36° C.;
2) Heart rate>90 per minute;
3) Respiration rate>20 per minute or $PaCO_2$>4.3 kPa;
4) White blood cell count>12,000, <4,000/$m^3$ or immature leukocytes>10%.

A doctor observed the patients' clinical findings and symptoms and made a judgment on the presence and absence of infection at the time of registry without requiring the blood culture results. It should be noted that the patients who had been confirmed to be suffering from SIRS other than the septic symptoms from the blood culture results after the registration were excluded.

The samples used for measuring the sCD14-ST level were prepared by collecting the EDTA plasma samples from the patients immediately after admission, 24 hours later and 72 hours later, and storing them at −70° C. until the time of measurement. The expression "immediately after admission" refers to a time period of within six hours.

In addition, the severity after admission was determined using "Acute Physiology And Chronic Health Score II" (APACHEII), "Glasgow Coma Scale" (GCS), "Sepsis-related Organ Failure Assessment Score" (SOFA), and "Mortality in Emergency Department Sepsis" (MEDS).

The prognosis was determined on the day of the patient's death within 30 days after admission to an emergency hospital, or on the day when the patient was either transferred to an intensive care unit (ICU), or subjected to mechanical ventilation or renal replacement therapy (for example, dialysis). When the patient was discharged from the hospital within 30 days, the survival status was verified by a phone call 30 days later.

Example 1

Measuring Method of sCD14-ST

The measurement of sCD14-ST was carried out by modifying the method described in Example 7-(1) of Japanese Patent No. 4040666. More particularly, a polyclonal antibody (S68 antibody) labeled with alkaline phosphatase (ALP) and a monoclonal antibody (F1031-8-3 antibody) immobilized on magnetic particles (manufactured by JSR) were used, and the measurement was carried out using an automated chemiluminescent enzyme immunoassay analyzer (PATHFAST; manufactured by Mitsubishi Chemical Medience Corporation). The polyclonal antibody (S68 antibody) labeled with alkaline phosphatase (ALP) was prepared by linking a Fab' fraction of the polyclonal antibody (S68 antibody) with ALP by a maleimide method. CPD-star (manufactured by Applied Biosystems) was used as the luminescent substrate.

The measurement was carried out as follows. A sample was reacted with the antibody immobilized on magnetic particles and the ALP-labeled antibody, to form a complex composed of sCD14-ST contained in the sample and both antibodies. The complex was collected by a magnetic body to remove the unbound ALP-labeled antibody from the reaction mixture. The luminescent substrate was added to detect the amount of the luminescence as the sCD14-ST level.

Example 2

Relationship Between sCD14-ST Level and Survival Rate

Figure 1:
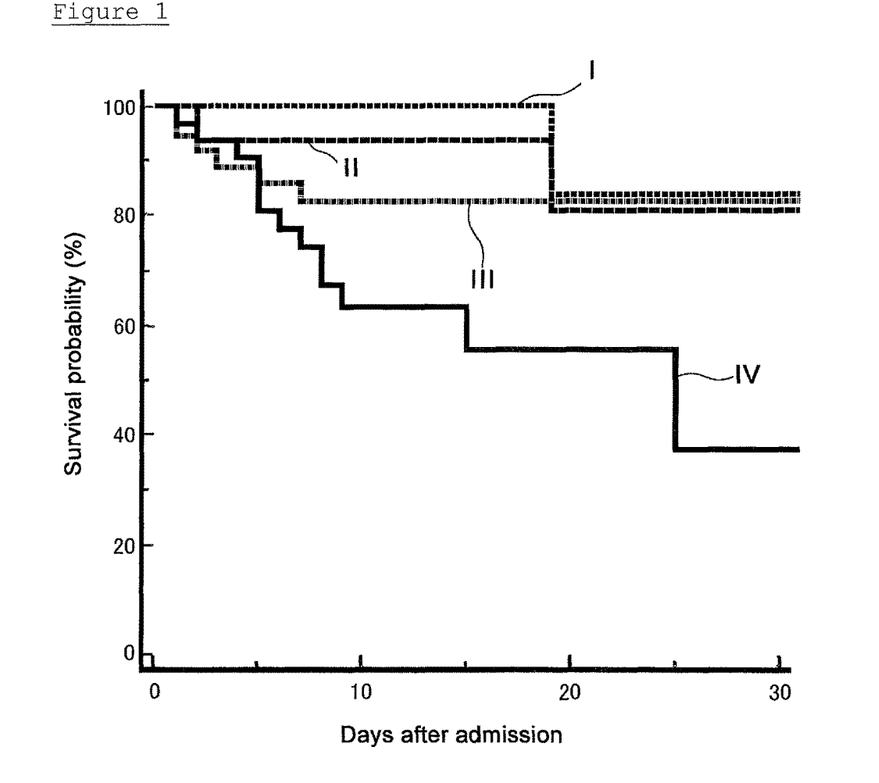
FIG. 1 is a graph showing the relationship between the sCD14-ST level in the plasma samples collected from the patients (146 individuals) with suspected sepsis at the time of admission and the survival rate within 30 days of admission. The sCD14-ST levels in groups I to IV are 177-512 pg/mL (group I), 524-927 pg/mL (group II), 950-1,810 pg/mL (group III), and 1,858 pg/mL or more (group IV), respectively.

The relationship between the sCD14-ST level in the plasma samples collected from the patients (146 individuals) at the time of admission with suspected sepsis and the survival rate within 30 days of the admission is shown in FIG. 1. The sCD14-ST level was measured in accordance with the method descrbed in Example 1. In FIG. 1, the horizontal axis indicates a number of days lapsed after the admission of a patient. The vertical axis indicates the survival rate (the lower the survival rate, the higher the mortality rate).

The patients were classified into four groups for analysis based on the sCD14-ST levels [177-512 pg/mL (group I in FIG. 1), 524-927 pg/mL (group II), 950-1,810 pg/mL (group III), and 1,858 pg/mL or more (group IV)]. As a result, the survival rate was reduced as the sCD14-ST level increased, and the survival rate in the patient group IV which exhibited an sCD14-ST level of 1,858 pg/mL or more at the time of admission was 35% (significance between the group III and group IV: $P<0.0005$). From the above results, it became evident that the death risk of sepsis patients can be predicted by the sCD14-ST level.

Example 3

Figure 2:
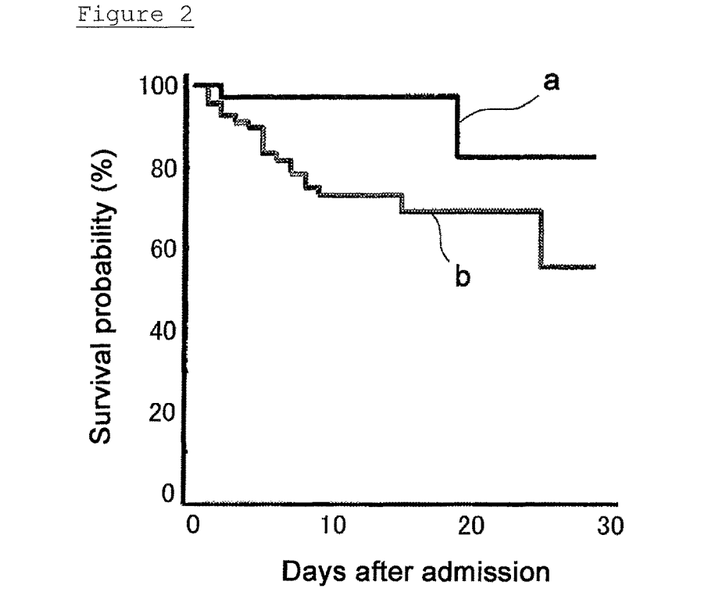
FIG. 2 is a graph showing the relationship between the sCD14-ST level in the plasma samples collected from the patients (146 individuals) with suspected sepsis at the time of admission and the survival rate within 30 days of admission. The threshold value is set to 920 ng/mL, and the patient group which exhibited a lower value than the threshold value is classified as group a, and the patient group which exhibited the threshold value or higher is classified as group b.
Figure 3:
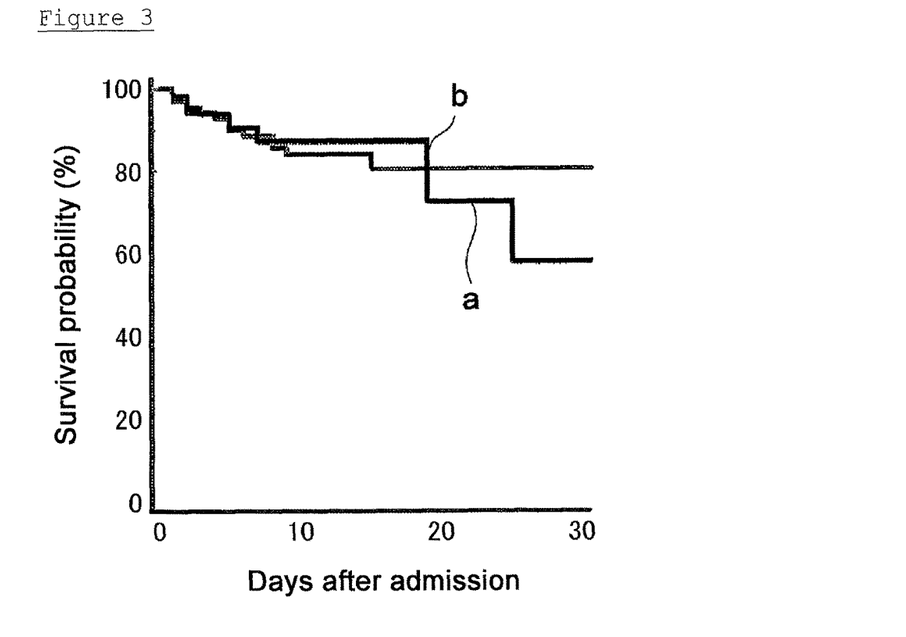
FIG. 3 is a graph showing the relationship between the procalcitonin (PCT) level in the plasma samples collected from the same patients of FIG. 2 at the time of admission and the survival rate within 30 days of admission. The threshold value is set to 1.86 ng/mL, and the patient group which exhibited a lower value than the threshold value is classified as group a, and the patient group which exhibited the threshold value or higher is classified as group b.

Comparative Evaluation of Survival Rates Predicted by Procalcitonin (PCT) Level and sCD14-ST Level The relationship between the sCD14-ST level in the plasma samples collected from the patients (146 individuals; the same as those in Example 2) with suspected sepsis at the time of admission and the survival rate within 30 days of the admission is shown in FIG. 2 (sCD14-ST), and the relationship between the PCT level in the plasma samples collected from the same patients at the time of admission and the survival rate within 30 days of the admission is shown in FIG. 3 (PCT), respectively. The sCD14-ST level was measured in accordance with the method described in Example 1. A reagent exclusively used for the measurement by the Kryptor automated analyzer (Brahms, Henningsdorf, Germany) was used for measuring the PCT level. The survival rates are shown when the threshold values were defined as 920 ng/mL for the sCD14-ST level and 1.86 ng/mL for the PCT level. As these threshold values, the medians of measured values of the registered patients at the time of admission were used. The patient group which exhibited a lower value than the threshold value was classified as group a, and the patient group with a higher value than the threshold value was classified as group b. The horizontal axis indicates a number of days lapsed after the admission of a patient. The vertical axis indicates the survival rate (the lower the survival rate, the higher the mortality rate). It became evident that the sCD14-ST level can evaluate the survival rate with higher accuracy than the PCT level and can also predict the death risk.

Example 4

Comparative Evaluation of PCT Level and sCD14-ST level by ROC Analysis

Figure 4:
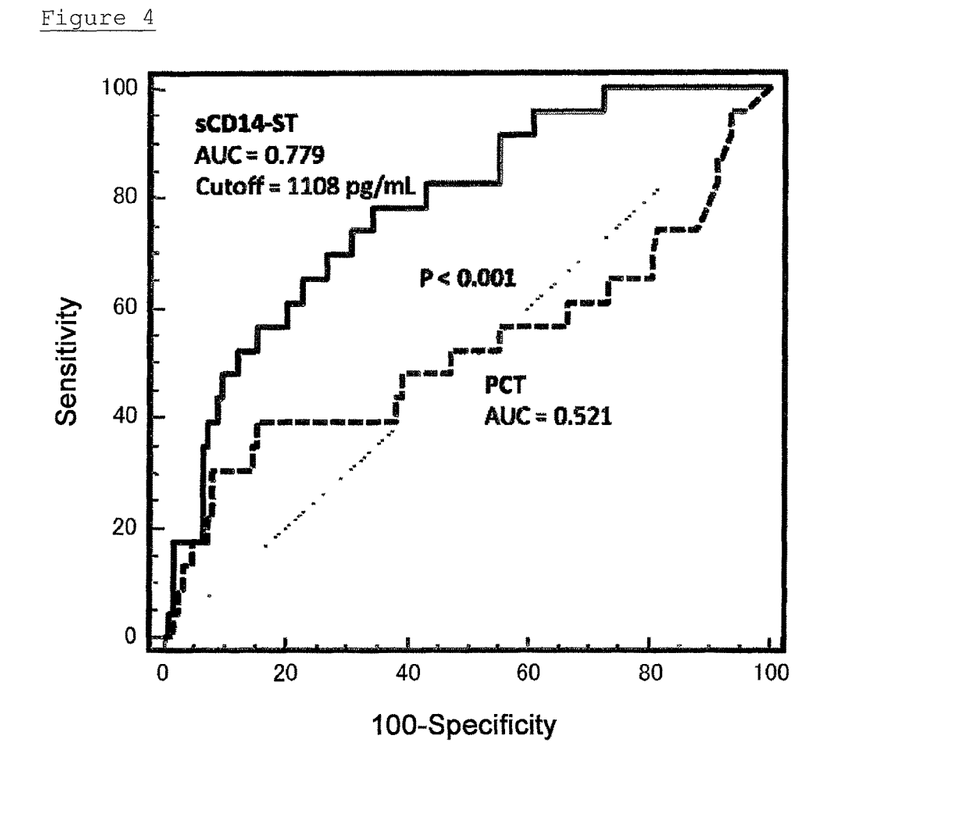
FIG. 4 is a graph showing the result of the receiver operating characteristic (ROC) analysis comparing the relationships between each of the sCD14-ST level and the PCT level in the plasma samples collected from the patients (146 individuals) with suspected sepsis at the time of admission and the mortality rate within 30 days of admission.

The sCD14-ST level and the PCT level in the plasma samples collected from the patients (146 individuals; the same as those in Example 2) with suspected sepsis at the time of admission were measured, and an ROC analysis was carried out to compare the mortality rate within 30 days of admission with each of the sCD14-ST level and the PCT level. The sCD14-ST level was measured in accordance with the method described in Example 1. A reagent exclusively used for measurement by the Kryptor automated analyzer (Brahms, Henningsdorf, Germany) was used for measuring the PCT level. In FIG. 4, the horizontal axis indicates "100 -(specificity)" and the vertical axis indicates the "sensitivity".

The area under the curve (AUC) for the sCD14-ST level was 0.779, which was larger than the AUC (0.521) for the PCT level. Although PCT has been approved by the FDA in the United States as a marker capable of predicting the severity level of sepsis, it was confirmed from the above result that the prediction by the sCD14-ST level was more accurate.

Example 5

Figure 5:
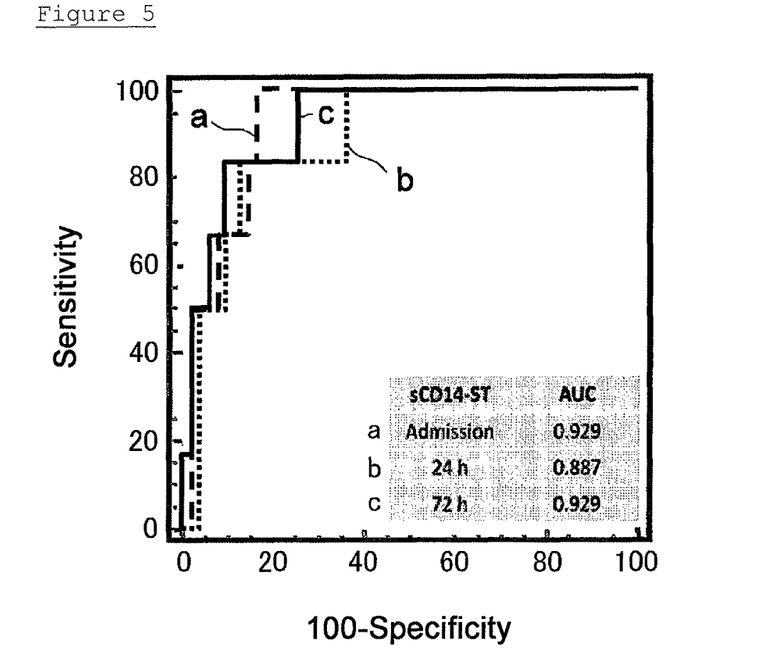
FIG. 5 is a graph showing the result of the ROC analysis comparing the mortality rate within 30 days of admission and the sCD14-ST levels at each point in time for blood collection, by collecting the plasma samples from the patients (146 individuals) with suspected sepsis at the time of admission (group a), 24 hours later (group b) and 72 hours later (group c).
Figure 6:
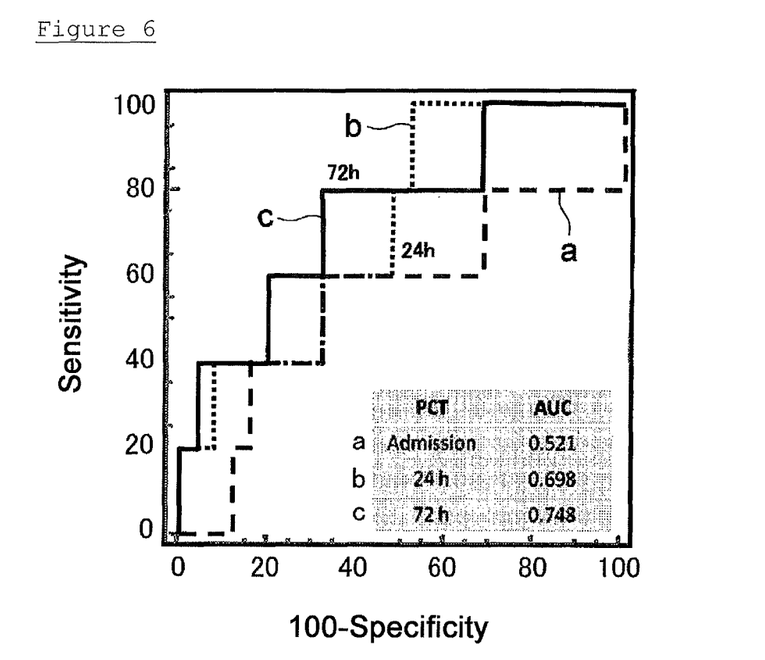
FIG. 6 is a graph showing the result of the ROC analysis comparing the mortality rate within 30 days of admission and the PCT levels at each point in time for blood collection, by collecting the plasma samples from the same patients of FIG. 5 at the time of admission (group a), 24 hours later (group b) and 72 hours later (group c).

Comparative Evaluation of PCT Level and sCD14-ST Level at Each Point in Time for Blood Collection within 72 Hours After Admission of Sepsis patient and Survival Rate The plasma samples were collected from the patients who were suspected of sepsis at the time of admission, 24 hours later and 72 hours later, and an ROC analysis was carried out to compare the mortality rate within 30 days after admission with the sCD14-ST level and the PCT level at each point in time for blood collection. This evaluation was carried out for the patients (68 individuals for sCD14-ST, 32 individuals for PCT) of which the data were obtained at all points in time for blood collection. The sCD14-ST level was measured in accordance with the method described in Example 1. A reagent exclusively used for the measurement by the Kryptor automated analyzer (Brahms, Henningsdorf, Germany) was used for measuring the PCT level. The results are shown in FIG. 5 (sCD14-ST) and FIG. 6 (PCT). The AUC at the time of admission, the AUC after 24 hours and the AUC after 72 hours are indicated by the polygonal lines a, b and c, respectively. It was shown that the sCD14-ST level, when measured at any point in time within 72 hours, can stably predict the death risk of sepsis patients within 30 days after admission with high accuracy.

Example 6

Comparative Evaluation of PCT Level and sCD14-ST Level at Admission of Sepsis Patient and Prognosis In a small-scale clinical test carried out prior to Examples 2 to 5, the plasma samples were collected from the patients (68 individuals) at the time of admission who were suspected of sepsis, and an ROC analysis was carried out to compare the state of the patient (subjected to artificial respiration treatment, transferred to an intensive care unit (ICU), subjected to dialysis, or death) within 30 days after the admission with the sCD14-ST level and the PCT level. The sCD14-ST level was measured in accordance with the method described in Example 1. A reagent exclusively used for measurement by the Kryptor automated analyzer (Brahms, Henningsdorf, Germany) was used for measuring the PCT level. The AUC value obtained by the ROC analysis is shown in Table 1. The results show that the sCD14-ST level was superior to the PCT level in predicting the risk for any of the indicators, and was also capable of predicting the risk for dialysis and death with considerably high accuracy.

TABLE 1

| Marker | State | | | |
| --- | --- | --- | --- | --- |
| | Artificial respiration treatment | Dialysis | Transfer to ICU | Death |
| PCT | 0.578 | 0.576 | 0.611 | 0.517 |
| sCD14-ST | 0.611 | 0.882 | 0.646 | 0.838 |

INDUSTRIAL APPLICABILITY

The present invention can be used for predicting the prognosis (especially the death risk) of patients suspected of having sepsis.

Although the present invention has been described with reference to specific embodiments, various changes and modifications obvious to those skilled in the art are possible without departing from the scope of the appended claims.

The invention claimed is:

1. A method for predicting a prognosis of sepsis and treating sepsis, the method comprising:
    measuring an sCD14-ST level in a sample collected from a human patient suspected of having sepsis or a sepsis human patient, said sample being selected from the group consisting of whole blood, plasma and serum;
    predicting a prognosis of sepsis of the human patient when the sCD14-ST level is higher compared to that of a healthy individual; and
    treating the human patient for sepsis with administration of a renal replacement therapy based upon the predicted prognosis of sepsis.

2. The method according to claim 1, wherein the sCD14-ST level is correlated with a quantile group, which is determined in which patients are classified and differentiated based on sepsis severity in advance, in the predicting step.

3. The method according to claim 1, wherein the sCD14-ST level is measured by an immunological measuring method.

4. The method according to claim 1, wherein the human patient is treated with antibiotics based on the predicted prognosis.

5. The method according to claim 1, wherein sepsis is treated by the use of a member selected from the group consisting of antimicrobial agents, fluid therapy, vasoconstrictors, cardiac drugs, steroid therapy, blood preparations, blood sugar control, blood purification methods, surgery, endotoxin adsorption therapy, and γ-globulin preparations.

6. The method according to claim 2, wherein the quantile level is a threshold value.

7. The method according to claim 6, wherein the threshold value is 920 pg/mL.

8. The method according to claim 2, wherein the quantile level is a member selected from level 1 of 177-512 pg/mL, level 2 of 524-927 pg/mL, level 3 of 950-1810 pg/mL, and level 4 of 1858 pg/mL or more.

9. The method of claim 3, wherein the immunological method comprises a polyclonal antibody labeled with alkaline phosphatase and a monoclonal antibody.

10. The method of claim 9, wherein the monoclonal antibody is a F1031-8-3 antibody immobilized on magnetic particles.

11. The method of claim 1, wherein the prediction is a prediction of a mortality rate within 5 to 30 days of admission.

* * * * *

SEQUENCE LISTING

```
<160> NUMBER OF SEQ ID NOS: 2

<210> SEQ ID NO 1
<211> LENGTH: 11
<212> TYPE: PRT
<213> ORGANISM: Homo sapiens

<400> SEQUENCE: 1

Thr Thr Pro Glu Pro Cys Glu Leu Asp Asp Glu
1               5                   10

<210> SEQ ID NO 2
<211> LENGTH: 16
<212> TYPE: PRT
<213> ORGANISM: Homo sapiens

<400> SEQUENCE: 2

Arg Val Asp Ala Asp Ala Asp Pro Arg Gln Tyr Ala Asp Thr Val Lys
1               5                   10                  15
```